(12) United States Patent
Peuckert et al.

(10) Patent No.: US 8,293,959 B2
(45) Date of Patent: Oct. 23, 2012

(54) PURIFICATION OF AN AROMATIC FRACTION CONTAINING ACETYLENES BY SELECTIVE HYDROGENATION OF THE ACETYLENES

(75) Inventors: Cornelius Peuckert, Dinslaken (DE); Christian Lambernd, Olfen (DE); Ulrich Niggemeyer, Marl (DE); Klaus Koester, Wuppertal (DE)

(73) Assignee: ISP Investment Inc., Wilmington, DE (US)

( * ) Notice: Subject to any disclaimer, the term of this patent is extended or adjusted under 35 U.S.C. 154(b) by 257 days.

(21) Appl. No.: 12/707,034

(22) Filed: Feb. 17, 2010

(65) Prior Publication Data

US 2010/0217053 A1  Aug. 26, 2010

(30) Foreign Application Priority Data

Feb. 17, 2009  (EP) .................................... 09153049

(51) Int. Cl.
*C07C 5/08* (2006.01)
(52) U.S. Cl. ......... 585/259; 585/250; 585/260; 585/263
(58) Field of Classification Search .......................... None
See application file for complete search history.

(56) References Cited

U.S. PATENT DOCUMENTS

| 3,917,737 | A * | 11/1975 | Yoo .............................. 585/277 |
| 5,504,268 | A | 4/1996 | Van Der Aalst et al. |
| 6,365,792 | B1 | 4/2002 | Stapf et al. |
| 6,747,181 | B1 | 6/2004 | Bosman et al. |
| 2002/0004622 | A1 | 1/2002 | Dai et al. |
| 2003/0233017 | A1 * | 12/2003 | Gelbein et al. ................ 585/258 |
| 2004/0176651 | A1 | 9/2004 | Molinier et al. |
| 2004/0232049 | A1 * | 11/2004 | Dath et al. ..................... 208/143 |
| 2004/0260131 | A1 * | 12/2004 | Bergmeister et al. ......... 585/259 |
| 2005/0033099 | A1 | 2/2005 | Ryu et al. |
| 2005/0090701 | A1 * | 4/2005 | Gelbein et al. ................ 585/259 |
| 2006/0063954 | A1 * | 3/2006 | Lowe et al. .................... 585/259 |
| 2006/0173224 | A1 | 8/2006 | Putman et al. |
| 2010/0152034 | A1 * | 6/2010 | Johnson et al. ............... 502/324 |
| 2011/0054227 | A1 * | 3/2011 | Cheung et al. .................. 585/16 |
| 2011/0319684 | A1 * | 12/2011 | Li et al. ........................ 585/270 |

FOREIGN PATENT DOCUMENTS

| EP | 1369465 A2 * | 12/2003 |
| GB | 264845 | 5/1928 |
| GB | 2053959 | 2/1981 |

OTHER PUBLICATIONS

EP, European Search Report, European Application No. 10153683.7 (Mar. 22, 2010).

* cited by examiner

*Primary Examiner* — Tam M Nguyen
(74) *Attorney, Agent, or Firm* — William J. Davis; Thompson Hine LLP

(57) ABSTRACT

A process for purification of an aromatic fraction containing acetylenes as impurities by selective hydrogenation of the acetylenes by means of a catalyst containing nickel or palladium at a temperature of not more than about 60° C. is described.

17 Claims, No Drawings

PURIFICATION OF AN AROMATIC FRACTION CONTAINING ACETYLENES BY SELECTIVE HYDROGENATION OF THE ACETYLENES

Acetylene is produced, among other processes, in hydrocarbon cracking processes such as the partial oxidation process (company BASF) and the electrical arc process (company ISP). These high temperature processes are not very selective and result in a wide variety of by-products. Besides hydrogen and soot, a wide variety of hydrocarbons such as aromatics, higher acetylenes, alkenes, and alkanes, are formed, of which the aromatic fraction is of special commercial interest as feedstock for gasoline or chemical processes.

The crack gas resulting from the arc process is separated in a multi-stage separation process using different absorption liquids for selective separation of different hydrocarbon fractions. In the Linde separation process, the C5-C6 hydrocarbons are absorbed in cold methanol and separated as an organic fraction containing a high proportion of benzene and other aromatic compounds (oil benzene). This oil benzene contains less than 20%, usually up to 15% of higher acetylenes. Examples of these higher acetylenes are vinylacetylene, diacetylene, methyldiacetylene, vinyldiacetylene, and phenylacetylene. The higher acetylenes tend to polymerise, particularly at higher temperatures (>40° C.) forming highly reactive polymers or, in diluted form, highly viscous, hardly pumpable mixtures. This effect requires, on the one hand, regular, costly and time consuming cleaning of the equipment and, on the other hand, prevents a further chemical use of the raw benzene other than incineration due to its uncontrolled polymerisation reaction.

While the selective hydrogenation of acetylenes to unsaturated hydrocarbons with Pd catalysts is well known in the art and widely used in industry, hydrogenation by means of Ni catalysts also leads to hydrogenation of —C≡C— bonds so that finally C—C bonds are obtained, and also the aromatic rings will be hydrogenated. To achieve economic conversion rates, the hydrogenation temperature must be above 50° C. at a hydrogen pressure>10 bar. Under these conditions, the higher acetylenes in the described oil benzene mixture already start to polymerise.

An object of the present invention was therefore to provide a process with which an aromatic fraction containing acetylenes can be purified by removing the acetylenes in such a manner that the aromatics are essentially not hydrogenated and essentially no polymerisation of the acetylenes occurs so that the purified aromatic fraction can be used as a raw material suitable for chemical or industrial applications.

Nickel and Palladium are well known catalysts for hydrogenation of benzene and other aromatic hydrocarbons. The task was to find a process wherein benzene and other aromatic hydrocarbons remain stable, and acetylenes and olefins are hydrogenated.

Surprisingly, it was found that the described oil benzene mixture can be converted to raw benzene for industrial or chemical applications by selective hydrogenation at moderate conditions both with Ni catalysts, in particular Raney Nickel, and Pd catalysts, with Ni catalysts being preferred.

Accordingly, the present invention provides a process for purification of an aromatic fraction containing acetylenes as impurities by selective hydrogenation of the acetylenes without hydrogenation of the aromatic fraction, i.e. without hydrogenation of the aromatic ring bonds, by means of a catalyst containing nickel or palladium at a temperature of not more than about 60° C.

The aromatic fraction or stream is a liquid mixture comprising one or more aromatic hydrocarbons. Preferred aromatic hydrocarbons are mononuclear aromatic compounds, i.e. benzene and benzene derivatives, in particular benzene substituted with one, two or more alkyl and/or alkenyl groups. The aromatic hydrocarbons preferably comprise 6 to 8 carbon atoms. Examples of the aromatic hydrocarbons are benzene, toluene, xylenes including o-xylene, m-xylene and p-xylene, and ethylbenzene. The aromatic fraction preferably comprises benzene and toluene or a mixture thereof.

The process of the present invention is appropriate for an aromatic fraction or stream which represents or which is based on a product or by-product of a manufacturing process and contains aromatic compounds and acetylenes. The process of the invention is particularly suitable for an aromatic fraction or stream which represents or is based on a by-product of an acetylene manufacturing process such as a hydrocarbon cracking process. The acetylene manufacturing process may, for instance, be a partial oxidation process or an electrical arc process or any other process suitable for acetylene production.

As mentioned above, many acetylene manufacturing processes result in a wide variety of hydrocarbons as by-products such as aromatics, higher acetylenes, alkenes and alkanes so that a more or less complex separation process is required. In general, an aromatic fraction including higher acetylenes is obtained from these separation processes as a by-product which is suitable as the starting material for the process of the present invention.

For instance, a particularly suitable by-product, namely an aromatic fraction, as a starting material for the process of the present invention is obtained when the crack gas resulting from an acetylene production by an arc process is separated in a multi-stage separation process using different absorption liquids for selective separation of different hydrocarbon fractions. Thus, in the Linde separation process the C5-C6 hydrocarbons are absorbed in cold methanol and separated, resulting in an organic fraction containing high amounts of benzene and/or toluene and optionally other aromatics (so-called "oil benzene"). This oil benzene contains less than 20% by weight and usually up to 15% by weight of higher acetylenes. Examples of these higher acetylenes are vinylacetylene, diacetylene, methyldiacetylene, vinyldiacetylene, and phenylacetylene. In general, the content of aromatic compounds in said aromatic fraction (oil benzene) is in a range of from about 5 to 50% by weight, preferably from about 10 to 45% by weight and more preferably from 20 to 40% by weight. The oil benzene may comprise other organic compounds and/or solvents as discussed below. This oil benzene is particularly suitable as a starting material for the process of the present invention. Optionally, a solvent as discussed below is added to the oil benzene before hydrogenation.

While the by-product of acetylene production discussed above is a preferred basis for the aromatic fraction or stream to be treated in accordance with the process of the present invention, other aromatic fractions or streams including acetylenes of other origin are suitable for the process of the invention as well. Since the aromatic fraction or stream used as a starting material for the process of the invention is usually a by-product or product of manufacturing processes which are not very selective, the aromatic fraction or stream may comprise a mixture of different compounds with respect to the aromatic hydrocarbons and the acetylenes and also with respect to other compounds of different chemical nature which may be included, generally in minor amounts.

The aromatic fraction or stream containing acetylenes may optionally comprise a solvent or a mixture of different solvents, and in a preferred embodiment the aromatic fraction or stream containing acetylenes comprises a solvent or a mixture of different solvents. Depending on the conditions which are employed in the separation step of the manufacturing process, in particular, in the acetylene manufacturing process, in order to obtain an aromatic fraction or stream which includes acetylenes as impurities, this aromatic fraction or stream obtained as a by-product may or may not comprise a solvent or a mixture of solvents. A solvent may be introduced during the separation process into the aromatic fraction or stream e.g. as an extractant. Said by-product, whether or not a solvent or a mixture of solvents is included, may be used as such as the aromatic fraction or stream to be purified according to the present invention. Alternatively, a solvent or a mixture of solvents may be added to the by-product obtained before the aromatic fraction or stream is selectively hydrogenated according to the process of the invention.

Any suitable solvent known to person skilled in the art may be used as the solvent included in the aromatic fraction or stream. Examples of suitable solvents are hydrocarbons, e.g. octane and hexane, water, alkanols, e.g. methanol, ethanol, n-propanol and n-butanol and isomers thereof, and mixtures thereof. Preferred solvents are alkanols, in particular methanol, and ethanol, and mixtures of methanol and water or ethanol and water. Methanol/water and ethanol/water mixtures used as solvent preferably have a water content in the range of 5 to 20% by weight based on the total weight of the mixture.

Aromatic hydrocarbons, such as benzene, toluene and xylenes may also be used as solvents. Contrary to the aromatic hydrocarbons contaminated with acetylenes contained in the aromatic fraction or stream to be purified, the aromatic hydrocarbons added as a solvent are relatively pure products, in particular they do not comprise acetylenes as impurities, but of course after addition of an aromatic hydrocarbon solvent the aromatic hydrocarbons derived from the contaminated aromatic fraction or stream and the aromatic hydrocarbons derived from the solvent cannot be distinguished from each other except for the case where the "contaminated" aromatic hydrocarbon and the aromatic hydrocarbon solvent are different from each other.

An advantage of the use of aromatic solvents may be that the product obtained in the purification process of the invention can be used as such without the need for subsequent separation of solvent. A disadvantage may be that also a part of the solvent will be hydrogenated and residues of acetylenes still remain after processing in accordance with the present invention so that also the "pure" solvent gets contaminated.

In general, a main purpose of the solvent, if used, is dilution of the aromatic fraction or stream which is used as the feed for selective hydrogenation in the process of the present invention. The solvent may also serve for better control of the reaction heat generated. In particular, it is preferred that the concentration of the acetylenes in the aromatic fraction or stream to be selectively hydrogenated according to the process of the invention should not be too high as will be explained below in detail. Further, the solvent may support or enhance the activity and/or selectivity of the catalyst to be used. In this regard the selection of the solvent may also depend on the catalyst system used. This relation is known to a skilled person who will be able to choose an appropriate combination of solvents and catalysts, if necessary.

The aromatic fraction or stream to be treated contains one or more acetylenes as impurities. The acetylenes include acetylene and acetylene derivatives. In particular, the acetylenes include or consist of higher acetylenes, i.e. acetylenes comprising more than 2 carbon atoms, preferably comprising at least 4 carbon atoms. The acetylenes comprise or consist of e.g. one or more compounds selected from the group consisting of substituted acetylenes, diacetylene and substituted diacetylenes. The substituted acetylenes and diacetylenes may comprise acetylene or diacetylene substituted with one or more groups selected from alkyl, e.g. $C_{1-4}$ alkyl such as methyl and ethyl, alkyl substituted with one or more aryls such as benzyl, alkenyl, e.g. $C_{2-4}$ alkyl such as vinyl and allyl, and aryl which may be substituted with alkyl groups, e.g. methyl, such as phenyl or tolyl. Examples of higher acetylenes are vinylacetylene, diacetylene, methyldiacetylene, vinyldiacetylene, and phenylacetylene or mixtures thereof. These higher acetylenes are common by-products of acetylene production.

Moreover, the aromatic fraction or stream may contain other by-products as impurities such as alkenes, alkanes or cycloalkanes in minor amounts. Examples are propane, butanes, cyclopentanes or olefins such as propene and butanes.

The amount of acetylenes in the aromatic fraction or stream may vary within wide ranges. However, if the amount of acetylenes is more than 20% by weight, polymerisation reactions of acetylenes tend to occur to a significant degree which disturbs the purification process. The amount of acetylenes in the aromatic fraction or stream to be selectively hydrogenated in the process of the present invention is suitably at least about 0.01% by weight, preferably at least about 0.1% by weight, more preferably more than 1% by weight or more than 3% by weight and still more preferably more than 5% by weight or more than 10% by weight, based on the total weight of the aromatic fraction or stream which is to be selectively hydrogenated in the process of the invention. Moreover, the amount of acetylenes in the aromatic fraction or stream to be selectively hydrogenated in the process of the invention is less than about 20% by weight, and preferably less than about 15% by weight, based on the total weight of the aromatic fraction or stream which is to be selectively hydrogenated in the process of the invention. Hence, the amount of acetylenes in the aromatic fraction or stream is preferably in the range of from 10 to 15% by weight, based on the total weight of the aromatic fraction or stream which is to be selectively hydrogenated in the process of the invention.

If the aromatic fraction or stream which is obtained as a by-product from an acetylene manufacturing process comprises relatively high amounts of acetylenes, it may be appropriate to add a solvent to the fraction or stream before selective hydrogenation in order to lower the concentration of acetylenes in the aromatic fraction or stream to be selectively hydrogenated so that the acetylenes concentration is within the above mentioned ranges.

By diluting the aromatic fraction or stream of the starting material such as the oil benzene by adding a solvent, the concentration of the acetylenes in the aromatic fraction or stream can be adjusted to the preferred ranges. For instance, a solvent may be optionally added to the starting material so that the solvent content in the aromatic fraction to be selectively hydrogenated in the process of the invention is from 0 to about 85% by weight, preferably from about 55 to about 80% by weight, based on the aromatic fraction or stream to be hydrogenated. Suitable solvents are those discussed above.

The amount of aromatic hydrocarbons in the aromatic fraction or stream may vary within wide ranges. In general, the amount of aromatic hydrocarbons in the aromatic fraction or stream to be selectively hydrogenated by the process of the invention is at least about 1% by weight, preferably at least about 4 or 5% by weight and more preferably at least about 10% by weight based on the total weight of the aromatic fraction or stream which is to be selectively hydrogenated by the process of the invention. As noted above, the amount of aromatic hydrocarbons also includes the aromatic hydrocarbons added as a solvent, if used. The amount of the aromatic hydrocarbons may vary considerably depending on the type of solvent used. The amount of the aromatic hydrocarbons excluding optionally added aromatic solvents may be less than about 30% by weight, preferably less than about 20% by weight, based on the total weight of the aromatic fraction or stream which is to be selectively hydrogenated in the process of the invention.

The amount of non-aromatic olefin compounds depends on the processes from which the aromatic fraction or stream is derived, but is preferably less than 5% by weight and usually significantly less than 5% by weight, e.g. less than 3% by weight, based on the total weight of the aromatic fraction or stream which is to be selectively hydrogenated in the process of the invention. The total amount of aromatic olefin compounds such as styrene is preferably less than 7% by weight, more preferably less than 5% by weight, based on the total weight of the aromatic fraction or stream which is to be selectively hydrogenated in the process of the invention.

The aromatic fraction or stream containing acetylenes as impurities is subjected to a selective hydrogenation of the acetylenes by means of a catalyst containing at least one of nickel and palladium at a temperature of not more than about 60° C. The hydrogenation is selective in that the acetylene triple bonds are essentially hydrogenated to single bonds or hydrogenated to such an extent that only minor amounts of acetylenic or olefinic bonds remain, e.g. less than 0.35, preferably less than 0.15 and more preferably less than 0.1% by weight of acetylenes and olefins based on the product obtained after selective hydrogenation, whereas aromatic hydrocarbons are not hydrogenated or hydrogenated to such an extent that e.g. not more than 5% by weight, preferably less than 1% of the aromatic hydrocarbons contained in the starting feed are hydrogenated with respect to the bonds of the aromatic ring. Preferably, essentially all or all triple bonds are converted to single bonds, i.e. if at all only trace amounts, e.g. less than 0.05% by weight of acetylenes and olefins are contained in the product obtained after selective hydrogenation. Preferably the aromatic hydrocarbons are not or essentially not hydrogenated with respect to the bonds of the aromatic ring, i.e. if at all only in trace amounts, e.g. not more than 0.35% of the aromatic hydrocarbons contained in the starting feed are hydrogenated with respect to the bonds of the aromatic ring. In other words, the selective hydrogenation of the acetylene triple bonds to single bonds is almost quantitative, for example, at least 98% to 100% of the acetylene triple bonds are converted to single bonds, whereas the aromatic rings of the aromatic hydrocarbons are not hydrogenated, e.g. 0.35% by weight or less of the aromatic hydrocarbons contained in the aromatic fraction are hydrogenated with respect to the bonds of the aromatic ring.

As the catalyst containing at least one of nickel and palladium any known hydrogenation catalyst can be used, nickel containing catalysts being preferred. Such catalysts are commercially available. The catalyst preferably comprises at least one of nickel in metallic form and palladium in metallic form. The catalyst may be a supported catalyst or an unsupported catalyst. The catalyst is generally solid and a heterogeneous catalyst. The unsupported catalyst may be e.g. in the form of a powder, metal black (finely divided powder), sponge, or wire gauze. The support material used for the supported catalyst may be any material known for this purpose to those skilled in the art. Examples for suitable support materials are activated carbon, aluminas including activated aluminas, silica including activated silica, silica gel, silicates, zeolite, calcium carbonate, barium sulfate, and magnesia.

The catalyst may be modified by conventional procedures known by the skilled person such as partial inhibition by catalyst poisons, alloying with active or inactive metals and addition of oxide containing activators or inhibitors. The preparation of supported and unsupported Ni or Pd containing catalysts and the optional modification thereof is well-known in the art and a general overview can be found e.g. in Ullmanns Encyklopadie der technischen Chemie, $4^{th}$ edition, vol. 13, Verlag Chemie, p. 135 to 141 and p. 517 to 566. A doping of the catalyst, in particular the Ni catalyst, is usually not favourably. It is preferred that the catalyst in particular the Ni catalyst, is not inactivated, i.e. a catalyst not modified or doped for inactivation, e.g. with S, Se, Te or compounds thereof, is preferably used.

Preferred examples of the catalyst employed in the present invention are Raney-nickel, supported nickel and supported Pd wherein Raney-nickel and supported nickel is preferred. The support material on which nickel or palladium is supported may be e.g. activated carbon, aluminas including activated aluminas, silica including activated silica, silica gel, silicates, zeolite, calcium carbonate, barium sulfate, and magnesia. Favourable examples of supported catalysts are Ni/alumina, Pd/alumina and Pd/activated carbon.

The amount of the catalyst added to the aromatic fraction or stream to be hydrogenated can vary within wide ranges and depends on the type of catalyst, the specific composition of the fraction and streams and the conditions selected for the hydrogenation process. The catalyst concentration is e.g. about 0.01% by weight or more, preferably about 0.05% by weight or more and about 10% by weight or less, preferably about 5% by weight or less, based on the total weight of the aromatic fraction or stream in the reaction volume.

The selective hydrogenation of the acetylenes in the aromatic fraction or stream by means of the catalyst containing at least one of Ni and Pd can be carried out in a discontinuous or continuous manner. The selective hydrogenation is preferably carried out as a continuous process. In general, the process is a hydrogenation in the liquid phase. For selective hydrogenation, hydrogen is generally introduced into a reactor in which the aromatic fraction or stream is present and in contact with the catalyst, by forcing hydrogen gas into the reactor to achieve a determined hydrogen pressure, as is known in the art.

The reactor may be any suitable reactor generally known in the field of hydrogenation. Examples of reactor types are agitated tank, tubular reactor, stirred vessel cascade, bubble column and fluid bed. The catalytic hydrogenation is preferably carried out in a fixed bed reactor or in suspension, more preferably in suspension. Suitable slurry reactors for hydrogenation in suspension are agitated tanks or agitated tank cascades, bubble columns and fluidised bed reactors. The selective hydrogenation is more preferably effected in suspension in a loop reactor. The process of the invention is preferably a catalytic hydrogenation in suspension using Raney-Nickel as the catalyst. Fixed bed catalysis is also possible for which usually a supported nickel such as nickel supported on alumina is employed. A catalytic hydrogenation with Raney-nickel in suspension, wherein the aromatic fraction comprises methanol as a solvent is most preferred.

The selective hydrogenation is carried out a temperature of not more than about 60° C. The hydrogenation temperature is preferably less than about 55° C., preferably less than about 50° C., and more preferably less than about 45° C. As shown in the examples, it was found that the higher acetylenes can be even selectively hydrogenated at unusually low temperatures of less than about 40° C. or even less than about 35° C.

The hydrogen pressure used may vary depending on the other parameters such as temperature, catalyst type, reaction time etc., but the hydrogen pressure is generally not more than about 50 bar, preferably not more than about 30 bar, and more preferably not more than about 20 bar.

The reaction time used may vary depending on the other parameters such as temperature, pressure, type of catalyst etc., but the reaction time of the hydrogenation is generally not more than about 300 min, preferably not more than about 120 min and more preferably not more than about 90 min. In preferred embodiments, the reaction is completed after the reaction time, i.e. the composition of the reaction mixture remains essentially constant when the reaction time given above is elapsed.

In consideration of the above, the results of the selective hydrogenation can be optimised if at least one, preferably two or more, and more preferably all of the following conditions for the hydrogenation are satisfied:
Catalyst concentration: 0.01-10% by weight
Temperature: ≦60° C.; preferably ≦50° C.
Hydrogen pressure: ≦50 bar
Reaction time: ≦300 min; preferably ≦120 min
Acetylenes in feed: ≦20% by weight; preferably <15% by weight The present invention also envisages recycling of a part of the product or the whole product obtained by the selective hydrogenation according to the present invention. Thus, the aromatic fraction or stream may be subject to the selective hydrogenation according to the purification process two or more times. A part of the product obtained by the selective hydrogenation according to the present invention can also be added to an aromatic fraction or stream not yet treated so that the untreated aromatic fraction or stream will be "diluted" with respect to the acetylenes concentration before it is submitted to the selective hydrogenation. Of course, recycling of part of the product obtained by the selective hydrogenation into the starting feed for selective hydrogenation can be accomplished in a continuous manner.

The hydrogenation of the aromatic fraction according to the present invention results in a surprisingly selective hydrogenation of the acetylenes in the fraction or stream. Acetylene triple bonds are almost completely hydrogenated to single bonds, no acetylenes and olefins or only traces thereof are found in the product. Only very little of aromatic compounds in the fraction or stream are hydrogenated or the aromatic compounds are not at all hydrogenated. Polymerization reactions of the acetylenes are not determined.

Thus, the process of the invention is suitable for purifying feeds of aromatic material from acetylenes so that the purified feed can be used e.g. as a feedstock for gasoline or other chemical processes. The following examples are intended to illustrate the invention, but not to limit it in any way. Percentages given are by weight unless indicated otherwise.

EXAMPLES

Example 1

A mixture comprising 9% benzene, 4.5% toluene and 12% of higher acetylenes in methanol as a solvent is hydrogenated with Ni/Al2O3 as a catalyst in a fixed bed at a pressure of 15 bar and a temperature of 30° C. After 2 hours no acetylenes and no olefins can be found. Benzene and toluene are not hydrogenated.

Example 2

A mixture comprising 9% benzene, 4.5% toluene and 12% of higher acetylenes in methanol with 11% water as a solvent is hydrogenated with Ni/Al2O3 as a catalyst in a slurry at a pressure of 10 bar and a temperature of 60° C. After 35 min no acetylenes and traces of olefins can be found. Benzene and toluene are not hydrogenated.

Example 3

A mixture comprising 15% toluene and 13% of higher acetylenes in benzene as a solvent is hydrogenated with Ni/Al2O3 as a catalyst in a fixed bed at a pressure of 50 bar and a temperature of 30° C. After 1 hour no acetylenes and no olefins can be found. The losses of benzene and toluene are less than 0.5%.

Example 4

A mixture comprising 9% benzene, 4.5% toluene and 12% of higher acetylenes in methanol/11% water as a solvent was hydrogenated with Pd/A-Coal as a catalyst at a pressure of 10 bar and a temperature of 30° C. After 1 hour the concentration of acetylenes was 0.3% and traces of olefins are found. Benzene and toluene are not hydrogenated.

Example 5

A mixture comprising 9% benzene, 4,5% toluene and 12% of higher acetylenes in methanol as a solvent is hydrogenated with Pd/A-Coal as a catalyst at a pressure of 50 bar and a temperature of 50° C. After 30 min no acetylenes and no olefins can be found. 0.3% of benzene and toluene are hydrogenated.

Example 6

A mixture comprising 9% benzene, 4,5% toluene and 12% of higher acetylenes in ethanol as a solvent was hydrogenated with Pd/Al2O3 as a catalyst in a fixed bed at a pressure of 25 bar and a temperature of 25° C. After 30 min no acetylenes and no olefins can be found. Benzene and toluene were not hydrogenated.

Example 7

A mixture comprising 4.5% toluene and 19% of higher acetylenes in benzene as a solvent was hydrogenated with Pd/Al2O3 as a catalyst in a slurry at a pressure of 50 bar and a temperature of 60° C. After 2 hours no acetylenes and no olefins can be found. About 5% of benzene and toluene are hydrogenated. Coke is found.

Example 8

| | |
|---|---|
| Catalyst: | Raney-Nickel 30 g/l |
| Pressure: | 16 bar |
| Temperature: | 40° C. |
| Reaction time: | 30 min |
| Acetylene feed: | 4.0% C4H2 |
| | 0.9% C4H4 |
| Acetylene after reaction: | <0.02% |

Benzene and toluene did not react.

Example 9

| Catalyst: | Pd/C 5%, 0.5 g/l |
|---|---|
| Pressure: | 16 bar |
| Temperature: | 25° C. |
| Reaction time: | 100 min |
| Acetylene feed: | 4.0% C4H2 |
|  | 0.9% C4H4 |
| Acetylene after reaction: | 0.1% C4H2 |
|  | <0.02% C4H4 |

Benzene and toluene did not react.

The invention claimed is:

1. A process for purification of an aromatic fraction containing less than about 20% by weight of acetylenes as impurities by selective hydrogenation of the acetylenes, wherein the acetylene triple bonds are hydrogenated to single bonds by means of a catalyst containing nickel or palladium at a temperature of not more than about 60° C., wherein the product obtained after selective hydrogenation contains less than 0.35% by weight of acetylenes and olefins.

2. The process according to claim 1, wherein the aromatic fraction comprises at least about 5% by weight of aromatic hydrocarbons.

3. The process according to claim 1, wherein the aromatic fraction comprises one or more aromatic hydrocarbons selected from the group consisting of benzene, toluene and xylene.

4. The process according to claim 1, wherein the hydrogenation temperature is less than about 55° C.

5. The process according to claim 1, wherein the acetylenes comprise one or more acetylenes selected from the group consisting of substituted acetylenes, diacetylene and substituted diacetylenes.

6. The process according to claim 1, wherein the aromatic fraction is a by-product or is based on a by-product of acetylene production by means of a cracking process.

7. The process according to claim 1, wherein the catalyst comprises nickel.

8. The process according to claim 1, wherein the catalyst comprises at least one of Raney nickel, Ni supported on alumina, Pd supported on alumina and Pd supported on activated carbon.

9. The process according to claim 8, wherein the amount of catalyst is about 0.01 to about 10% by weight, based on the total weight of the aromatic fraction in the reaction volume.

10. The process according to claim 1, wherein the hydrogen pressure is not more than about 50 bar.

11. The process according to claim 1, wherein the reaction time of the hydrogenation is not more than about 120 min.

12. The process according to claim 1, wherein the aromatic fraction comprises a solvent.

13. The process according claim 1, wherein a solvent is added to an aromatic fraction obtained from a separation process before hydrogenation.

14. The process according to claim 12 or claim 13, wherein the solvent is selected from the group consisting of hydrocarbons, water, ethanol, methanol, methanol/water and mixtures thereof.

15. The process according claim 1, wherein the catalytic hydrogenation is carried out in a fixed bed reactor or in suspension.

16. The process according to claim 1, wherein the aromatic fraction comprises at least about 10% by weight of aromatic hydrocarbons.

17. The process according to claim 12, wherein the aromatic fraction comprises an alkanol or an alkanol/water mixture.

* * * * *